United States Patent
Kennedy et al.

(10) Patent No.: US 6,911,554 B2
(45) Date of Patent: Jun. 28, 2005

(54) ISOCYANO SUBSTITUTED POLYSTYRENE CARBONATE RESIN FOR USE IN 3 AND 4 COMPONENT CONDENSATION REACTIONS

(75) Inventors: April Kennedy, Boulder, CO (US); John A. Josey, Boulder, CO (US)

(73) Assignee: Array Biopharma Inc., Boulder, CO (US)

(*) Notice: Subject to any disclaimer, the term of this patent is extended or adjusted under 35 U.S.C. 154(b) by 192 days.

(21) Appl. No.: 10/337,579

(22) Filed: Jan. 7, 2003

(65) Prior Publication Data

US 2003/0225267 A1 Dec. 4, 2003

Related U.S. Application Data

(60) Provisional application No. 60/346,430, filed on Jan. 7, 2002.

(51) Int. Cl.⁷ .............................................. C07C 255/03
(52) U.S. Cl. .................. 558/398; 558/303; 558/388; 558/389
(58) Field of Search ................. 558/398, 303, 558/388, 389

(56) References Cited

PUBLICATIONS

I. Ugi, *Angew. Chem.* 1962, 74, 9 (attached is English translation of Abstract only).
I. Ugi et al., *Tetrahedron* 1995, 51, 139.
Ugi et al., *Tetrahedron,* 1999, 55, 7411.
Hulme et al., *Tetrahedron Lett.* 1998, 39, 1113.
Hulme et al., *Tetrahedron Lett.* 2000, 41, 1883.

*Primary Examiner*—Golam M M Shameem
(74) *Attorney, Agent, or Firm*—McDonnell Boehnen Hulbert & Berghoff

(57) ABSTRACT

This invention relates to compounds comprising isocyano derivatives tethered to solid supports for use in 3 and 4 component condensation reactions. The invention also relates to methods for synthesizing cyclic derivatives by a 3 and 4 component condensation reaction using the compounds of the invention.

6 Claims, No Drawings

ISOCYANO SUBSTITUTED POLYSTYRENE CARBONATE RESIN FOR USE IN 3 AND 4 COMPONENT CONDENSATION REACTIONS

This application claims the benefit of application Ser. No. 60/346,430 filed on Jan. 7, 2002.

BACKGROUND OF THE INVENTION

1. Field of the Invention

This invention relates to compounds for use in 3 and 4 component condensation reactions. The invention also relates to methods for synthesizing cyclic derivatives by the 3 and 4 component condensation reaction.

2. Description of the Related Art

The multi-component reaction (MCR) is a useful process for preparing large arrays of diverse compounds. In a typical multi-component reaction, three or more starting materials are reacted with one another simultaneously or almost simultaneously in a one-pot reaction. The process does not require the work up of intermediates.

Multi-component reactions in which one of the components is an isocyanide include the Passerini 3-component reaction (P-3CR); the Ugi 4-component reaction (U-4CR) [I. Ugi, *Angew. Chem.* 1962, 74, 9]; and the Ugi 4-component reaction with β-amino acids (U-4CR/β-AS) [I. Ugi et al., *Tetrahedron* 1995, 51, 139].

The Ugi/De-BOC/Cyclization (UDC) strategy has been employed in combination with isocyano compounds in a solution phase synthesis of constrained Ugi derivatives (Hulme et al., *Tetrahedron Lett.* 1998, 39, 1113). Conversion of Ugi products derived from (β-isocyano-ethyl)-alkyl carbonates to N-acylated α-amino acids and esters has been reported (Ugi et al., Tetrahedron, 1999, 55, 7411). The solution techniques are not resin bound and are therefore not useful for high speed synthesis because of purity problems. The solution/solid phase generation of γ-lactam analogs has also been reported. This procedure tethers N-BOC aldehydes of an Ugi multi-component reaction to a solid support. BOC removal and treatment with base affords γ-lactams. (Hulme et al., *Tetrahedron Lett.* 2000, 41, 1883). This method suffers in that it results in the formation of primary amide by-products.

Cyclic derivatives, such as diketopiperazine and diketobenzodiazepine ring systems, are found in a wide variety of compounds having diverse medicinal utility. Based upon the usefulness of these compounds, it would generally be advantageous to have structures and methods of rapidly and efficiently synthesizing structurally diverse derivatives of these and other cyclic compounds, as well as libraries containing large numbers of such compounds. The present invention meets these and other needs.

SUMMARY OF THE INVENTION

This invention relates to solid supported compounds that are used in the 3 and 4 component condensation reaction. The invention also relates to methods of preparing cyclic derivatives, such as diketopiperazines or diketobenzodiazepines, using the supported compounds of the invention.

Typically, the methods of the invention employ a multi-component reaction for the synthesis of intermediate compounds on solid supports. Cyclization of the intermediate compounds results in formation of the desired cyclic derivative, as well as release of the compound from the solid support.

In one embodiment, the invention provides compounds for use in a 3 and 4 component condensation reaction, having the formula I:

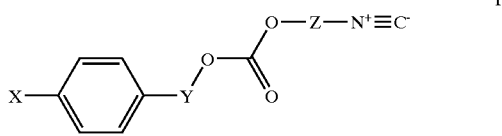

wherein X is a solid support, Y and Z are independently alkyl, aryl, heteroaryl, aralkyl, heteroaralkyl, acyl, alkoxyl, aryloxyl, mercapto, alkylthio, arylthio, amino or amido.

In another embodiment, the invention is a method of synthesizing a cyclic derivative by the 3 or 4 component condensation reaction, comprising combining an aldehyde or ketone, an amine, and an aminocarboxylic acid with a compound of formula I under conditions whereby a support bound derivative is formed, and cyclizing the support bound derivative to form the cyclic derivative, followed by release of the cyclic derivative from the support.

In yet another embodiment, the invention is a method of synthesizing a cyclic derivative, such as a diketopiperazine compound or a diketobenzodiazepine compound, comprising the steps of forming an isocyano derivative on a solid support; combining an aldehyde or ketone, an amine, and an aminocarboxylic acid with the isocyano derivative under conditions whereby a bisamide is formed on the solid support; and cyclizing the support bound bisamide to form a cyclic derivative, followed by release of the cyclic derivative from the support.

In still another embodiment, the invention is directed to compounds of formula II(a), II(b) and II(c);

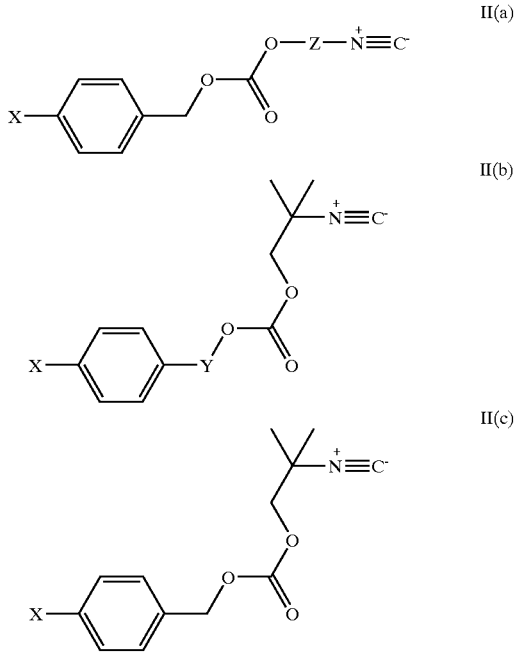

wherein X, Y and Z are as defined for formula I.

In a further embodiment, the invention is directed to a method of preparing a compound of formula II, as depicted in Example 1, below.

DETAILED DESCRIPTION OF THE INVENTION

The convertible isonitrile resins described herein offer resin bound isonitrile functionalities that can be used in 3 and 4 component condensations without any primary amide by-product formation as seen with the immobilized cyclohexenyl isonitrile resin. The isonitirile resins of the invention are much less expensive to manufacture than the safety catch linker isonitrile resin. These resins can be made in essentially two steps, so they are also much easier to manufacture than either the immobilized cyclohexenyl isonitrile resin or the safety catch-linker isonitrile resin. This invention also provides methods of using isonitrile resins to synthesize cyclic derivatives.

Definitions

The following definitions are set forth to illustrate and define the meaning and scope of the various terms used to describe the invention herein.

"Acyl" denotes groups —C(O)R, where R is alkyl or substituted alkyl, aryl, or substituted aryl as defined below.

"Alkyl" or "lower alky" refer interchangeably to a cyclic, branched or straight chain, alkyl group of one to eight carbon atoms. This term is further exemplified by such groups as methyl, ethyl, n-propyl, i-propyl, n-butyl, t-butyl, i-butyl (or 2-methylpropyl), cyclopropylmethyl, i-amyl, n-amyl, and hexyl. Preferred groups are methyl, sec-butyl, iso-butyl and iso-propyl. "Substituted lower alkyl" refers to lower alkyl as just described including one or more functional groups such as lower alkyl, aryl, aralkyl, acyl, halogen, hydroxyl, amino, mercapto and the like. These groups may be attached to any carbon atom of the lower alkyl moiety. Preferred groups are 2-guanidinopropyl, 2-carboxymethyl, 2-amidomethyl, thiomethyl, 2-carboxyethyl, 2-amidoethyl, 3-imidazolylmethyl, 4-aminobutyl, 3-hydroxyl-4-aminobutyl, 2-(methylthio)ethyl, hydroxymethyl and 1-hydroxyethyl.

"Alkenyl" generally refers to a lower alkyl substituent having one or more double bonds, such as ethenyl and substituted forms thereof. "Alkynyl" refers herein to a lower alkyl substituent having one or more triple bonds, such as ethynyl. "Substituted alkenyl" and "substituted alkynyl" refer to an alkenyl or an alkynyl as just described including one or more functional groups such as lower alkyl, aryl, aralkyl, acyl, halogen, hydroxyl, amino, acylamino, acyloxy, alkoxyl, mercapto and the like.

"Alkoxyl" denotes the group —OR, where R is lower alkyl, substituted lower alkyl, aryl, substituted aryl, aralkyl or substituted aralkyl as defined below.

"Alkylthio" denotes the group —SR, where R is lower alkyl, substituted lower alkyl, aryl, substituted aryl aralkyl or substituted aralkyl as defined below.

"Amido" denotes the group —C(O)NRR', where R and R' may independently be hydrogen, lower alkyl, substituted lower alkyl, aryl, substituted aryl as defined below or acyl.

"Amino" denotes the group NRR', where R and R' may independently be hydrogen, lower alkyl, substituted lower alkyl, aryl, substituted aryl as defined below or acyl.

"Amino Acid Derivative" as used herein, refers generally to both natural and unnatural amino acids, preferably an α- or β-amino acid, which may or may not be modified by the addition of one or more protecting groups, such as 9-fluorenylmethyloxycarbonyl (Fmoc), benzyl or t-butoxycarbonyl (BOC), and/or activating groups or by its coupling to a solid support.

"Aralkyl" refers to the group —R—Ar where Ar is an aryl group and R is straight-chain or branched-chain aliphatic group. Aralkyl groups can optionally be unsubstituted or substituted with, e.g., halogen, lower alkyl, lower alkoxy, lower alkylthio, trifluoromethyl, lower acyloxy, and hydroxy. Preferred aralkyl groups include benzyl, hydroxybenzyl, methylbenzyl, chlorobenzyl, bromobenzyl, iodobenzyl, thiobenzyl, aminobenzyl, napthylmethyl and hydroxynapthylmethyl.

"Aryl" or "Ar" refers to an aromatic carbocyclic group having at least one aromatic ring (e.g., phenyl or biphenyl) or multiple condensed rings in which at least one ring is aromatic, (e.g., 1,2,3,4-tetrahydronaphthyl, naphthyl, anthryl, or phenanthryl). Preferred substituents are phenyl and napthyl. "Substituted aryl" refers to aryl optionally substituted with one or more functional groups, e.g., halogen, lower alkyl, lower alkoxyl, lower alkylthio, trifluoromethyl, lower acyloxyl, hydroxyl and the like. Preferred groups include methylphenyl, chlorophenyl, iodophenyl, bromophenyl, 4-hydroxyphenyl, thiophenyl, 4-chlorothiophenyl, 2-methylthiophenyl and 4-methylsulfonylphenyl.

"Aryloxyl" denotes groups —OAr, where Ar is an aryl or substituted aryl group as defined below.

"Halogen" refers to fluorine, bromine, chlorine, and/or iodine atoms.

"Heteroaryl" or "HetAr" refers to an aromatic carbocyclic group having a single ring (e.g., pyridyl or furyl) or multiple condensed rings (e.g., naphthyridinyl, quinoxalyl, quinolinyl, indolizinyl or benzo[b]thienyl) and having at least one hetero atom, such as N, O or S, within the ring. "Substituted heteroaryl refers to heteroaryl substituted with, e.g., halogen, lower alkyl, lower alkoxy, lower alkylthio, trifluoromethyl, lower acyloxy, and hydroxy. Preferred heteroaryl groups include indolyl, methylindolyl, imidazolyl, N-methylimidazolyl and methylimidazolyl.

"Heteroarylalkyl" refers to the group —R-HetAr where HetAr is an heteroaryl group and R is straight-chain or branched-chain aliphatic group. Heteroarylalkyl groups can optionally be unsubstituted or substituted with, e.g., halogen, lower alkyl, lower alkoxyl, lower alkylthio, trifluoromethyl, lower acyloxy, and hydroxy. Preferred heteroaralkyl groups include 3-indolylmethyl and 2-imidazolylmethyl.

"Hydroxyl" refers to the group —OH.

A preferred compound of the invention is of the formula II

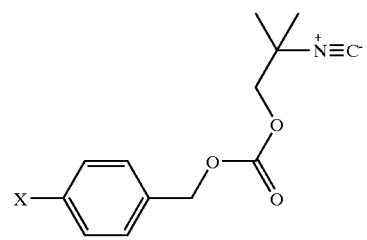

As depicted herein, X represents the un-illustrated portion of the solid support.

The Solid Support

Solid supports upon which the cyclic derivatives can be synthesized may include glass, latex, silica gel, cross-linked polystyrene and other similar polymers and resins, gold and other colloidal metal particles.

Preferred supports include Hydroxymethyl Polystyrene Resin (100–200 mesh) (substitution: 1.29 meq/g from Colorado Biotechnology Associates, Inc.).

Preferably, the solid support contains pendent alcohol groups which can be converted to a chloroformate for further reaction (see e.g., example 1, below). Alternatively, although less preferably, the alcohol can be converted to a p-nitrophenyl carbonate for further reaction.

The Isocyano Functionality

Introduction of an isocyano functional group onto the polymer support is done by reacting an isocyano containing compound with the support under conditions that provide coupling.

The isocyano containing compound should contain an isocyano functional group and at least one other functional group capable of coupling with the solid support. Example 2 depicts one example of an isocyano containing compound and Example 1 depicts coupling of this compound with the functionalized solid support. In these examples, the coupling functional groups on the support and the isocyano containing compound are, respectively, chloroformate and alkoxide.

The following examples are illustrative of the invention, but do not serve to limits its scope.

EXAMPLES

Example 1

The synthesis of (β-isocyanoethyl)-polystyrene carbonate resin is shown in Scheme 1.

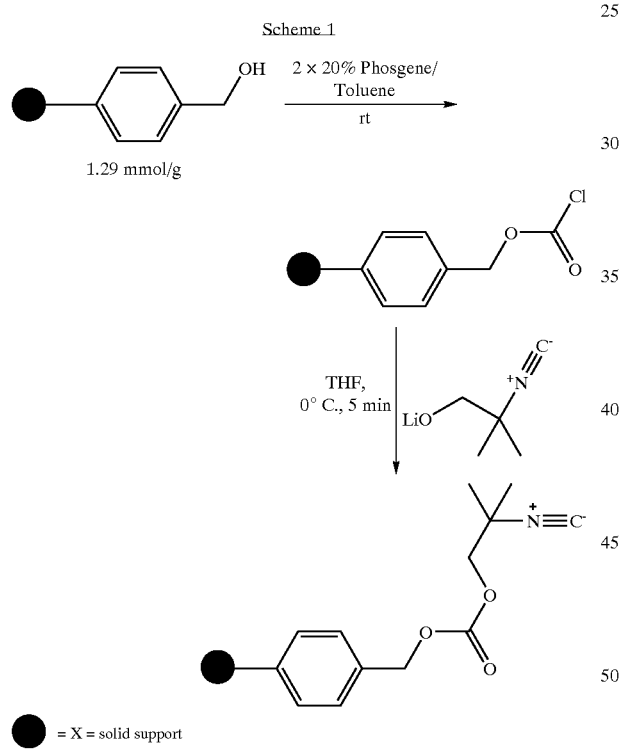

● = X = solid support 205 g of Hydroxymethyl Polystyrene Resin (100–200 mesh) (substitution: 1.29 meq/g from Colorado Biotechnology Associates, Inc.) is washed with 4 L of toluene and 2 L of pentane and then placed under high vacuum overnight for drying. The dry resin is then placed in a 3 necked 5 L round bottom flask fitted with an automatic overhead stir paddle. The resin is then swollen with 3 L of toluene (DriSolve). Next, a 20% phosgene in toluene solution (3 equiv., 410 mL) is added via an addition funnel with a steady flow rate of addition. Upon complete addition, the reaction is stirred for 30 minutes at room temperature. The resin is then filtered using a 3 L fritted (C) funnel and washed with 2 L of toluene (DriSolve). The resin is returned to the 3 necked 5 L round bottom flask and the reaction is repeated a second time. Upon filtration the second time, the resin is washed with 1 L of toluene and 1 L of THF. The resin is then returned to the 3 necked round bottom flask and diluted with 3 L of THF. The resin is then cooled to 0° C. in an ice/H$_2$O bath over 1 h. The lithium alcoholate (prepared in Scheme 2) is then cannulated in at a steady flow rate. Upon complete addition of the alcoholate, the reaction is stirred for 5 min and then filtered. The resin is washed with THF (1 L), MeOH (2 L), DCM (1 L), and pentane (1 L). The resin is then dried overnight under high vacuum. 234 g of resin were recovered and shown to have a loading of 0.87 mmol/g by microanalysis (Schwarzkopf Microanalytical Laobratory, Inc.). A trace amount of chlorine is found to be also present. IR 2150 cm$^{-1}$.

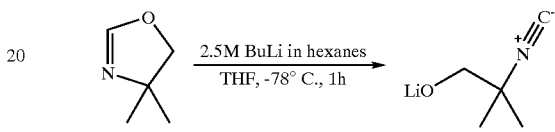

Scheme 2

To a 1 L flame dried round bottom flask are added 270 mL DriSolve THF and 26 g of 4,4-dimethyl-2-oxazoline (1 equivalent with respect to Hydroxymethyl Polystyrene Resin). The solution is cooled to −78° C. and a 2.5 M solution of BuLi in hexanes (127 mL, 1.2 equiv.) is added via syringe while vigorously stirring. The color dissipates at first but the solution stays dark orange upon complete addition. The reaction is stirred for 1 h at −78° C. under N$_2$ before cannulation into the resin bound chloroformate (see Scheme 1).

Example 2

A multi-component reaction utilizing the (β-isocyanoethyl)-polystyrene carbonate resin prepared in example 1 is illustrated in Scheme 3.

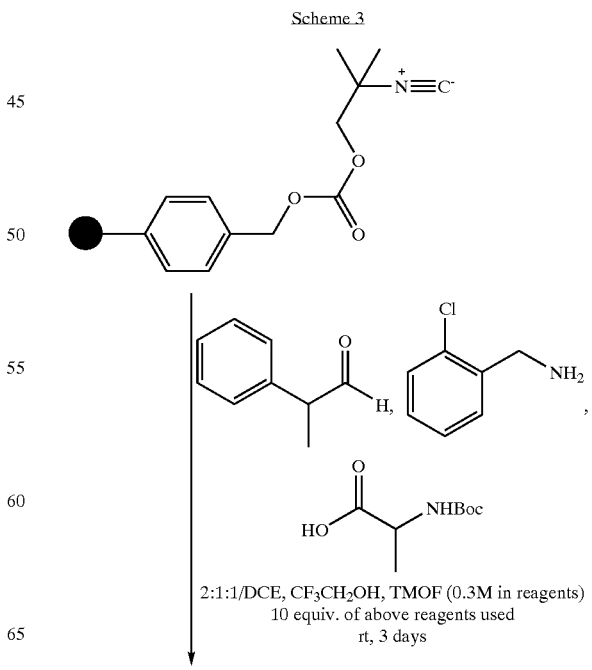

Scheme 3

-continued

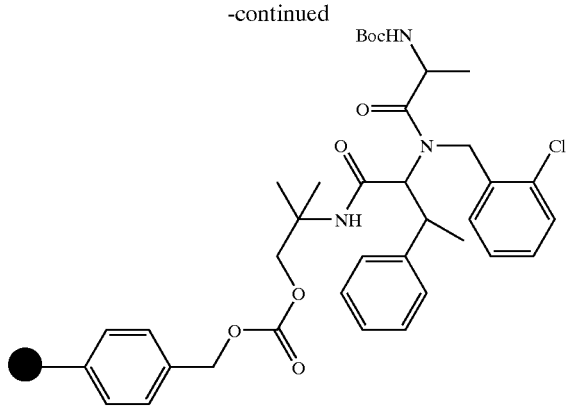

A 1.2 M solution of 2-chlorobenzylamine (1.1 mmol, 133 μL) and 2-phenylpropionaldehyde (1.1 mmol, 146 μL) in trimethyloithoformate (tmof) is made and allowed to react for 30 minutes. 126 mg (110 μmol) of (β-isocyanoethyl) alkylcarbonate resin (substitution:0.87 meq/g (see Scheme 1)) is swollen for 15 minutes in 1.75 mL of DCE in a 5 mL Bohdan fritted reaction tube. The 1.2 M solution of imine in tmof is then added to the resin followed by a 1.2 M solution of Boc-DL-alanine in trifluoroethanol (tfe). The reaction is then shaken at room temperature for 3 days. The reaction is then filtered and washed with DCE (3×2 mL), MeOH (3×2 mL), and pentane (2 mL). Absence of isonitrile stretch in the IR.

Example 3

Cyclization and release of the cyclic derivative from the support are illustrated in Scheme 4.

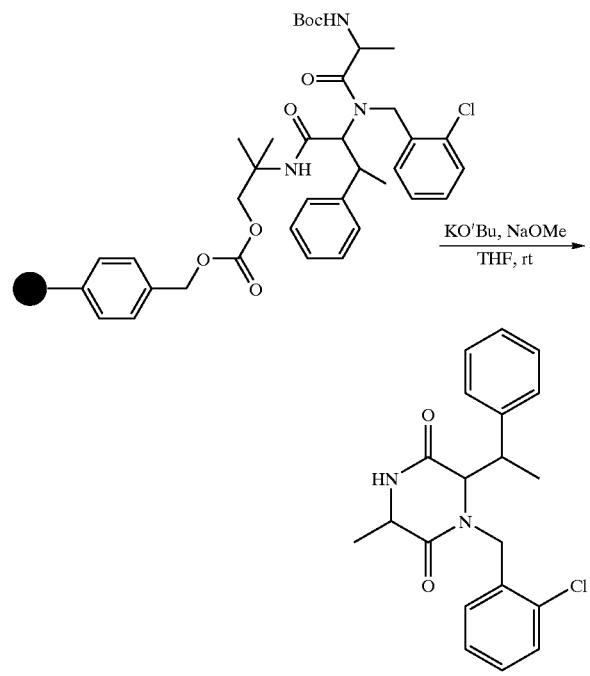

The resin bound 4 component condensation product (see Scheme 3) is swollen in THF (1.8 mL). 1 M KO'Bu in THF (2 equiv, 220 μL) is added and the reaction is shaken at room temperature overnight. NaOMe (1 equiv) is then added and the reaction allowed to stir at room temperature for an additional 5 h. The reaction is then filtered into a test tube using a vac master and washed with THF (3×1 mL). The solution is transferred to a 20 mL round bottom flask and concentrated on a rotovap at 50° C. The sample is then triturated with DCM (4×500 μL). The triturate is then placed in a 10 mL round bottom flask and treated with 900 μL of TFA. The reaction is allowed to sit overnight at room temperature. The reaction is then concentrated on the rotovap and redissolved in 2 mL of TVF. TMA-Carbonate (Silicycle, 0.73 mmol/g, 2 equiv) is added to the reaction and allowed to stir for 2 h. Next, isocyanate-3 (Silicycle, 1.3 mmol/g, 1.5 equiv) is added to the reaction and allowed to stir for an additional 2 h. The reaction is then filtered through a fritted Bohdan tube into a test tube and transferred to a 10 mL round bottom flask and concentrated to give the diketopiperazine product. MS pos APCI hfba/acn infusion showed m/z=357.

Example 4

Preparation of a benzodiazepine product by a multicomponent reaction is illustrated in Scheme 5.

Scheme 5

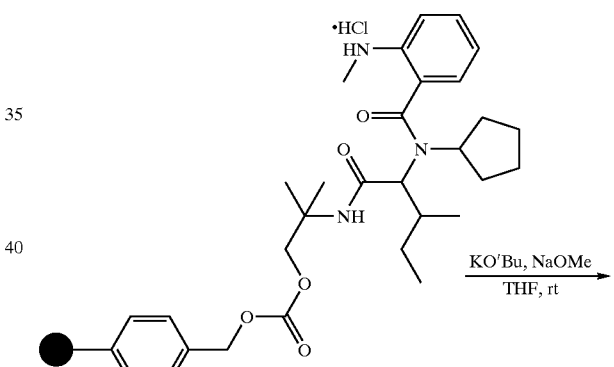

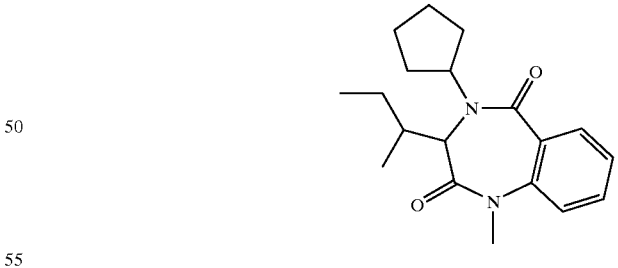

The same procedure as followed for Schemes 3 and 4 is followed here, except 2-methylbutyraldehyde (1.1 mmol, 118 μL) is used instead of 2-phenylpropionaldehyde, the hydrochloric salt of N-methylanthranilic acid (1.1 mmol, 206 mg) is used instead of BOC-DL-alanine, and cyclopentylamine (1.1 mmol, 108 μL) is used instead of 2-chlorobenzylamine, in the four component condensation reaction using the isonitrile resin shown in Scheme 1. This gave the benzodiazepinedione product. MS pos esi m/z=315.

What is claimed is:

1. A compound of the formula:

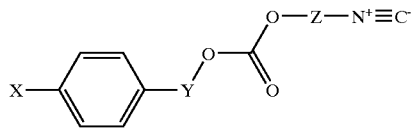

wherein X is a solid support selected from glass, latex, silica gel, polymer and colloidal metal particle; Y and Z are independently alkyl, aryl, heteroaryl, aralkyl, heteroaralkyl, acyl, alkoxyl, aryloxyl, mercapto, alkylthio, arylthio, amino or amido.

2. The compound of claim 1 wherein Y is alkyl.

3. The compound of claim 1 wherein Z is alkyl.

4. The compound of claim 1 wherein Y is methylene and Z is isobutylene.

5. A compound according to claim 1 having the formula:

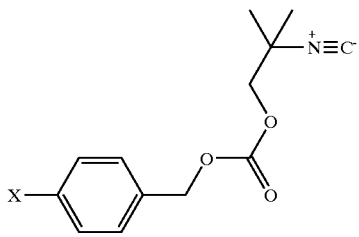

6. A compound according to claim 1 wherein the compound is a (β-isocyanoethyl)-polystyrene carbonate resin.

* * * * *